(12) United States Patent
Nabutovsky et al.

(10) Patent No.: US 10,322,290 B2
(45) Date of Patent: Jun. 18, 2019

(54) SYSTEMS AND METHODS FOR INTEGRATING TEMPORARY INDUCED DYSSYNCHRONY THERAPY WITH CARDIAC RESYNCHRONIZATION THERAPY

(71) Applicant: PACESETTER, INC., Sylmar, CA (US)

(72) Inventors: Yelena Nabutovsky, Mountain View, CA (US); Jennifer Rhude, Carbondale, IL (US); Edward Karst, Los Angeles, CA (US); Taraneh G. Farazi, San Jose, CA (US)

(73) Assignee: Pacesetter, Inc., Sylmar, CA (US)

( * ) Notice: Subject to any disclaimer, the term of this patent is extended or adjusted under 35 U.S.C. 154(b) by 15 days.

(21) Appl. No.: 15/628,454

(22) Filed: Jun. 20, 2017

(65) Prior Publication Data

US 2018/0361166 A1 Dec. 20, 2018

(51) Int. Cl.
| | |
|---|---|
| *A61N 1/00* | (2006.01) |
| *A61N 1/39* | (2006.01) |
| *A61N 1/368* | (2006.01) |
| *A61N 1/362* | (2006.01) |

(52) U.S. Cl.
CPC ......... *A61N 1/3962* (2013.01); *A61N 1/3627* (2013.01); *A61N 1/3682* (2013.01); *A61N 1/3684* (2013.01); *A61N 1/3688* (2013.01)

(58) Field of Classification Search
CPC .... A61N 1/3627; A61N 1/3622; A61N 1/368; A61N 1/3682; A61N 1/3684; A61N 1/36842; A61N 1/36843
See application file for complete search history.

(56) References Cited

U.S. PATENT DOCUMENTS

2013/0304149 A1* 11/2013 Kass .................... A61N 1/3627
607/17

* cited by examiner

*Primary Examiner* — Scott M. Getzow

(57) ABSTRACT

The present disclosure provides systems and methods for integrating cardiac resynchronization therapy (CRT) and temporary induced dyssynchrony (TID) therapy. An implantable cardiac device includes one or more pulse generators coupled to a plurality of electrodes, and a controller communicatively coupled to the one or more pulse generators and configured to cause the one or more pulse generators to apply a combination of CRT and TID therapy to a patient's heart via the plurality of electrodes in accordance with at least one protocol.

18 Claims, 3 Drawing Sheets

SYSTEMS AND METHODS FOR INTEGRATING TEMPORARY INDUCED DYSSYNCHRONY THERAPY WITH CARDIAC RESYNCHRONIZATION THERAPY

A. FIELD OF THE DISCLOSURE

The present disclosure relates generally to cardiac stimulation systems, and more particularly to an implantable cardiac device that integrates temporary induced dyssynchrony therapy with cardiac resynchronization therapy.

B. BACKGROUND ART

Heart failure (HF) is a debilitating, end-stage disease in which abnormal function of the heart leads to inadequate blood flow to fulfill the needs of the body's tissues. Typically, the heart loses propulsive power because the cardiac muscle loses capacity to stretch and contract. Often, the ventricles do not adequately fill with blood between heartbeats, and the valves regulating blood flow may develop leaks, allowing regurgitation or backflow of blood. The impairment of arterial circulation deprives vital organs of oxygen and nutrients. Fatigue, weakness, and inability to carry out daily tasks may result. Not all HF patients suffer debilitating symptoms immediately. Some may live actively for years. Yet, with few exceptions, the disease is relentlessly progressive. As HF progresses, it tends to become increasingly difficult to manage.

Using temporary induced dyssynchrony (TID) therapy to create regular, periodic asynchrony in HF patients without underlying dyssynchrony has been shown to facilitate improvement of the cardiac chamber function, cellular function, and cardiac reserve. Specifically, at least some known TID therapy, such as pacemaker-induced transient asynchrony (PITA) therapy that uses a pacemaker to induce asynchrony, involves using right ventricular (RV) pacing to induce forced ventricular asynchrony in a patient's heart at regular intervals (e.g., for a period of six hours every night for six weeks). One concept behind TID therapy is that the heart may benefit from "exercise" (i.e., forcing the heart into ventricular asynchrony), similar to other muscles in the body.

For HF patients that do have existing dyssynchrony, cardiac resynchronization therapy (CRT) pacing is an established treatment. Specifically, CRT pacing includes the delivery of multiple ventricular pacing pulses to improve cardiac function by increasing the synchrony of the ventricle. Traditionally, CRT has included biventricular (BiV) pacing in which one pacing pulse is delivered to the left ventricle and one pacing pulse is delivered to the right ventricle. Recently, multi-point pacing (MPP) has been implemented as an option that may provide increased clinical benefits compared to BiV pacing. MPP includes delivering two pacing pulses to the left ventricle and one pacing pulse to the right ventricle. The delivery of the extra left ventricular (LV) pacing pulse in MPP may further increase synchrony and thus further improve clinical response.

Both TID therapy and CRT are beneficial due to the cellular response associated with a transition from asynchrony to synchrony. Patients receiving CRT generally already have natural dyssynchrony, and CRT induces synchrony. In contrast, TID therapy, specifically PITA therapy, induces periodic asynchrony via pacing and a transition to synchrony when the pacing stops. However, TID therapy may provide benefits to CRT patients, but the delivery of the TID therapy may need to be altered to achieve those benefits.

BRIEF SUMMARY OF THE DISCLOSURE

In one embodiment, the present disclosure is directed to an implantable cardiac device for providing cardiac resynchronization therapy (CRT) and temporary induced dyssynchrony (TID) therapy. The implantable cardiac device includes one or more pulse generators coupled to a plurality of electrodes, and a controller communicatively coupled to the one or more pulse generators and configured to cause the one or more pulse generator to apply a combination of CRT and TID therapy to a patient's heart via the plurality of electrodes in accordance with at least one protocol.

In another embodiment, the present disclosure is directed to a computing device for use in an implantable cardiac device that includes one or more pulse generators coupled to a plurality of electrodes. The computing device includes a memory device, and a processor communicatively coupled to the memory device, the processor configured to cause the one or more pulse generators to apply a combination of cardiac resynchronization therapy (CRT) and temporary induced dyssynchrony (TID) therapy to a patient's heart via the plurality of electrodes in accordance with at least one protocol.

In another embodiment, the present disclosure is directed to a method for providing cardiac resynchronization therapy (CRT) and temporary induced dyssynchrony (TID) therapy. The method includes communicatively coupling one or more pulse generators to a controller, and causing the one or more pulse generators to apply a combination of CRT and TID therapy to a patient's heart via a plurality of electrodes in accordance with at least one protocol.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides systems and methods for integrating cardiac resynchronization therapy (CRT) and temporary induced dyssynchrony (TID) therapy. An implantable cardiac device includes a plurality of electrodes coupled to a pulse generator. A controller communicatively coupled to the pulse generator is configured to cause the pulse generator to apply a combination of CRT and TID therapy via the plurality of electrodes to a patient's heart in accordance with at least one protocol.

Figure 1A:
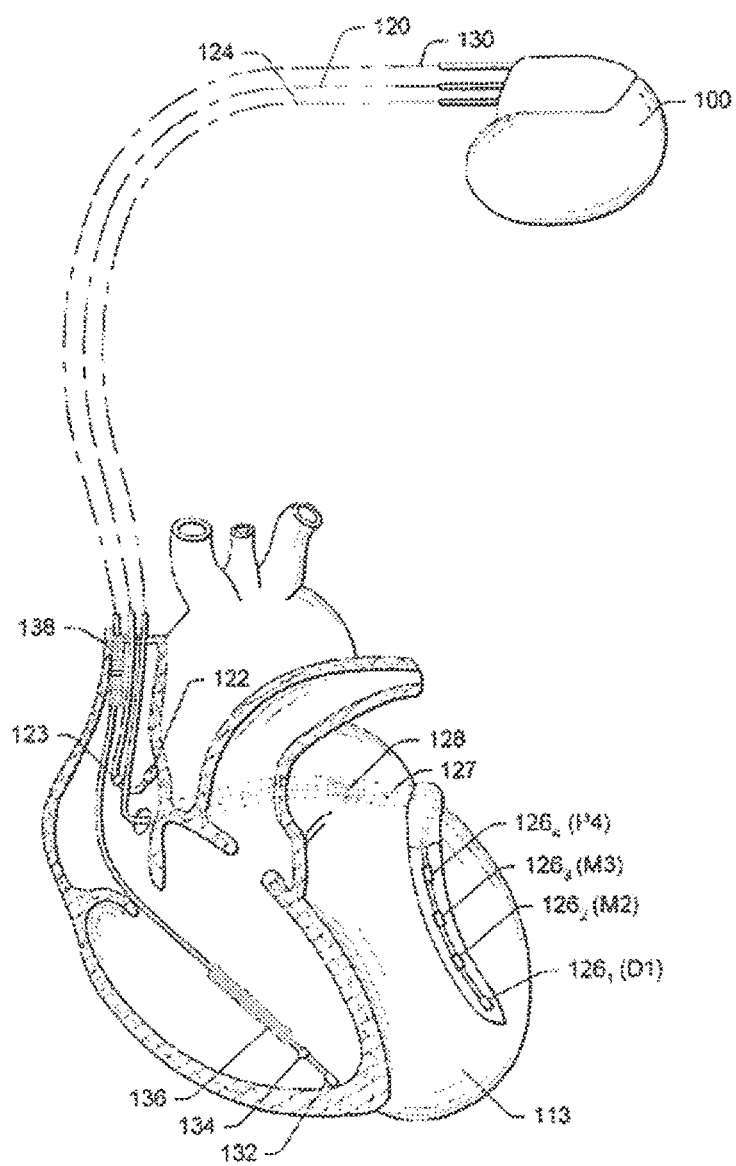
FIG. 1A is a simplified, partly cutaway view illustrating an implantable stimulation device in electrical communication with at least three leads implanted into a patient's heart for delivering multi-chamber stimulation and shock therapy and sensing cardiac activity.
Figure 1B:
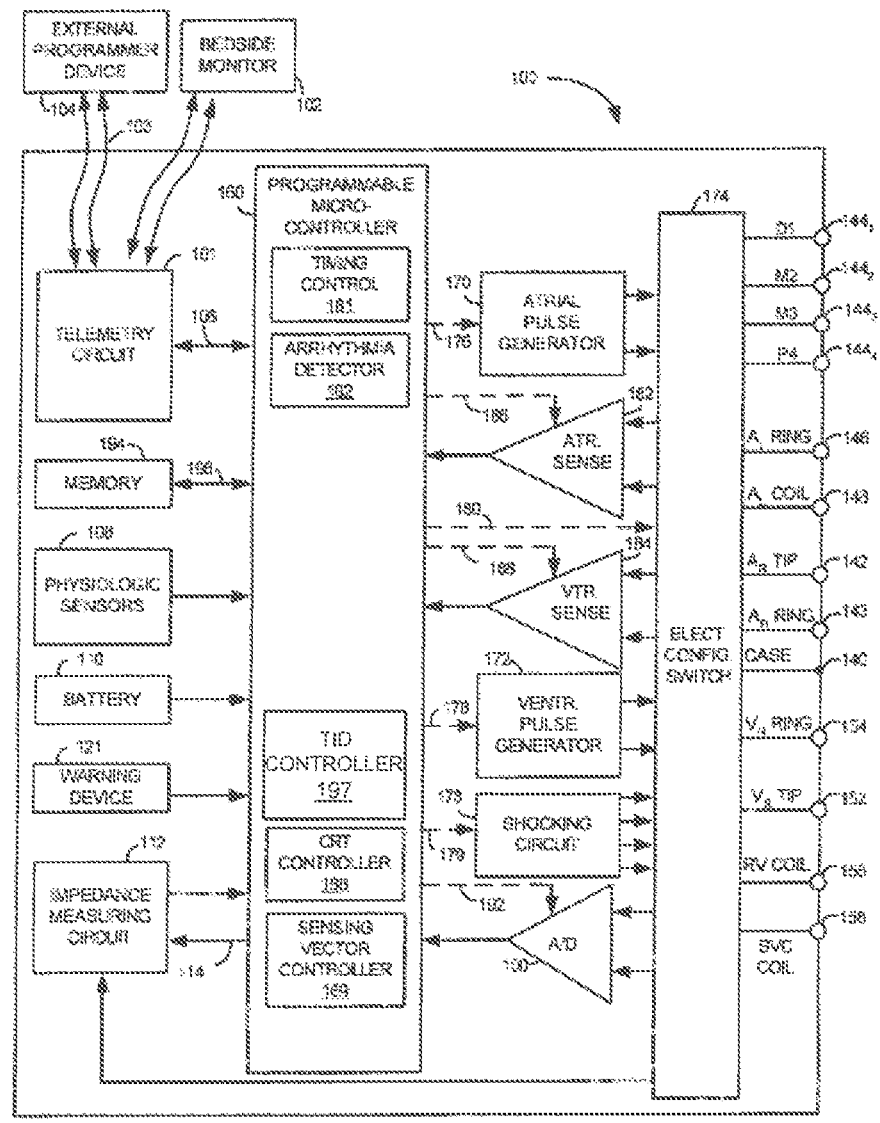
FIG. 1B is a functional block diagram of the multi-chamber implantable stimulation device of FIG. 1A, illustrating the basic elements that provide pacing stimulation, cardioversion, and defibrillation in four chambers of the heart.

With reference to FIGS. 1A and 1B, a description of an example pacemaker/implantable cardioverter-defibrillator (ICD) 100 will now be provided. FIG. 1A is a simplified block diagram of pacemaker/ICD 100, which is a dual-chamber stimulation device capable of treating both fast and slow arrhythmias with stimulation therapy, including cardioversion, defibrillation, and pacing stimulation, including multipoint pacing (MPP). To provide atrial chamber pacing stimulation and sensing, pacemaker/ICD 100 is shown in electrical communication with a heart 113 by way of a right atrial (RA) lead 120 having an atrial tip electrode 122 and an atrial ring electrode 123 implanted in the atrial appendage. Pacemaker/ICD 100 is also in electrical communication with heart 113 by way of a right ventricular (RV) lead 130 having, in this embodiment, a ventricular tip electrode 132, a RV ring electrode 134, a RV coil electrode 136, and a superior vena cave (SVC) coil electrode 138. Typically, RV lead 130 is transvenously inserted into the heart so as to place RV coil electrode 136 in the RV apex, and SVC coil electrode 138 in the superior vena cava. Accordingly, RV lead 130 is capable of receiving cardiac signals, and delivering stimulation in the form of pacing and shock therapy to the right ventricle (also referred to as the RV chamber).

To sense left atrial and ventricular cardiac signals and to provide left chamber pacing therapy, pacemaker/ICD 100 is coupled to a multi-pole left ventricular (LV) lead 124 designed for placement in the "CS region" for positioning a distal electrode adjacent to the left ventricle and/or additional electrode(s) adjacent to the left atrium (also referred to as the LA chamber). As used herein, the phrase "CS region" refers to the venous vasculature of the left ventricle, including any portion of the coronary sinus (CS), great cardiac vein, left marginal vein, left posterior ventricular vein, middle cardiac vein, small cardiac vein, and/or any other cardiac vein accessible by the CS. Accordingly, an example LV lead 124 is designed to receive, atrial and ventricular cardiac signals and to deliver left ventricular pacing therapy using a set of four LV electrodes $126_1$, $126_2$, $126_3$, and $126_4$ (thereby providing a quadra-pole lead), left atrial pacing therapy using at least a LA ring electrode 127, and shocking therapy using at least a LA coil electrode 128. In some embodiments, LV lead 124 includes LV electrodes $126_1$, $126_2$, $126_3$, and $126_4$, but does not include LA ring and coil electrodes 127 and 128. Such a lead can be, e.g., the Quartet™ left ventricular pacing lead developed by Abbott Laboratories, which includes four pacing electrodes on the left ventricular lead—enabling up to ten pacing configurations.

LV electrode $126_1$ is shown as being the most "distal" LV electrode (with relation to how far the electrode is from where LV lead 124 connects to pacemaker/ICD 100). For example LV electrode $126_1$ may be located at the apex of the left ventricle. LV electrode $126_4$ is shown as being the most "proximal" LV electrode. For example LV electrode $126_4$ may be located at the base of the left ventricle. LV electrodes $126_2$ and $126_3$ are shown as being "middle" LV electrodes, between distal and proximal LV electrodes $126_1$ and $126_4$. Accordingly, the four LV electrodes $126_1$, $126_2$, $126_3$, and $126_4$ can be referred to respectively as electrodes D1, M2, M3 and P4 (where "D" stands for "distal", "M" stands for "middle", and "P" stands from "proximal", and the numbers are arranged from most distal to most proximal). It is also possible that more or fewer LV electrodes are provided. However, for much of the remaining discussion, it will be assumed that the multi-pole LV lead 124 includes four LV electrodes $126_1$, $126_2$, $126_3$, and $126_4$ (i.e., LV electrodes D1, M2, M3 and P4, respectively).

LV electrodes $126_1$, $126_2$, $126_3$, and $126_4$ can be used to provide various pacing vectors and sensing vectors. Some of the vectors are intraventricular LV vectors (vectors between two LV electrodes); whereas others are interventricular vectors (e.g., vectors between an LV electrode and RV coil electrode 136). Below is a list of exemplary vectors that can be used for pacing and/or sensing using LV electrodes D1, M2, M3 and P4 with and without the RV coil electrode 136. In the following list, the first electrode in each row (i.e., the electrode to the left of the arrow) is assumed to be connected as the cathode, and the second electrode in each row (i.e., the electrode to the right of the arrow) is assumed to be connected as the anode, but that need not be the case, especially where neither electrode is a coil.

D1→RV coil
M2→RV coil
M3→RV coil
P4→RV coil
D1→M2
D1→P4
M2→P4
M3→M2
M3→P4
P4→M2

Alternative and/or additional vectors, other than those listed above, can be used for pacing and/or sensing. Although only three leads are shown in FIG. 1A, it should also be understood that additional leads (with one or more pacing, sensing, and/or shocking electrodes) might be used and/or additional electrodes might be provided on the leads already shown, such as additional electrodes on the RV or LV lead. It is also possible that less than three leads be used.

A simplified block diagram of internal components of pacemaker/ICD 100 is shown in FIG. 1B. While a particular pacemaker/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. A housing 140 for pacemaker/ICD 100, shown schematically in FIG. 1B, is often referred to as the "can", "case" or "case electrode" and may be programmably selected to act as the return electrode for all "unipolar" modes. Housing 140 may further be used as a return electrode alone or in combination with one or more of coil electrodes, 128, 136 and 138 for shocking purposes. Housing 140 further includes a connector (not shown) having a plurality of terminals, 142, 143, $144_1$-$144_4$, 146, 148, 152, 154, 156 and 158 (shown schematically and, for convenience, the names of the electrodes to which they are connected are shown next to the terminals). As such, to achieve RA sensing and pacing, the connector includes at least an RA tip terminal ($A_R$ TIP) 142 adapted for connection to the atrial tip electrode 122 and an RA ring ($A_R$ RING) electrode 143 adapted for connection to atrial ring electrode 123. To achieve left chamber sensing, pacing and shocking, the connector includes an LV tip terminal $144_1$ adapted for connection to the D1 electrode and additional LV electrode terminals 144$_2$, 144$_3$ and 144$_4$ terminals adapted for connection to the M2, M3 and P4 electrodes of quadra-pole LV lead 124.

The connector also includes an LA ring terminal (A$_L$ RING) 146 and an LA shocking terminal (A$_L$ COIL) 148, which are adapted for connection to LA ring electrode 127 and the LA coil (A$_L$ COIL) electrode 128, respectively. To support right chamber sensing, pacing and shocking, the connector further includes an RV tip terminal (V$_R$ TIP) 152, an RV ring terminal (V$_R$ RING) 154, an RV shocking terminal (V$_R$ COIL) 156, and an SVC shocking terminal (SVC COIL) 158, which are adapted for connection to ventricular tip electrode 132, RV ring electrode 134, RV coil electrode 136, and SVC coil electrode 138, respectively.

At the core of pacemaker/ICD 100 is a programmable microcontroller 160, which controls the various modes of stimulation therapy. As is well known in the art, microcontroller 160 (also referred to herein as a control unit or controller) typically includes a microprocessor, or equivalent control circuitry, designed specifically for controlling the delivery of stimulation therapy and may further include RAM or ROM memory, logic and timing circuitry, state machine circuitry, and I/O circuitry. Typically, microcontroller 160 includes the ability to process or monitor input signals (data) as controlled by a program code stored in a designated block of memory.

As shown in FIG. 1B, an atrial pulse generator 170 (controlled by a control signal 176) and a ventricular pulse generator 172 (controlled by a control signal 178) generate pacing stimulation pulses for delivery by RA lead 120, RV lead 130, and/or LV lead 124 via an electrode configuration switch 174. Microcontroller 160 includes timing control circuitry 161 to control the timing of the stimulation pulses, including, but not limited to, pacing rate, atrio-ventricular (AV) delay, interatrial conduction (AA) delay, interventricular conduction (VV) delay and/or intraventricular delay (e.g., LV1-LV2 delay). Timing control circuitry 161 can also keep track of timing of refractory periods, blanking intervals, noise detection windows, evoked response detection windows, alert intervals, marker channel timing, etc.

Microcontroller 160 further includes an arrhythmia detector 162 that can be utilized by pacemaker/ICD 100 for determining desirable times to administer various therapies. Additional components of the microcontroller may include a cardiac resynchronization therapy (CRT) controller 168 to control CRT and a temporary induced dyssynchrony (TID) controller 197 (described in detail below).

Microcontroller 160 is also shown as including a sensing vector controller 169 that can be used, e.g., to control the electrode configuration switch 174 (e.g., via control signals 180) to selectively connect specific electrode(s) to sensing circuits. 182 or 184 as a cathode or an anode, to achieve the various sensing vectors that are used to obtain intracardiac electrograms (IEGMs) in accordance with embodiments described herein. Where multiple sensing vectors are being used to obtain a plurality of IEGMs indicative of cardiac electrical activity at a plurality of ventricular regions, sensing circuit 184 may include multiple channels (e.g., duplicate circuitry) to enable sensing of more than one ventricular IEGM signal at the same time, and/or sensing circuit 184 may use time divisional multiplexing to sense more than one ventricular IEGM signal.

Depending upon the implementation, the various components of the microcontroller may be implemented as separate software modules or the modules may be combined to permit a single module to perform multiple functions. For example, CRT controller 168 and TID controller 197 may be combined. In addition, although shown as being components of the microcontroller, some or all of these components may be implemented separately from the microcontroller, using application specific integrated circuits (ASICs) or the like.

Switch 174 includes a plurality of switches for connecting the desired electrodes to the appropriate I/O circuits, thereby providing complete electrode programmability. Accordingly, switch 174, in response to a control signal 180 from microcontroller 160, determines the polarity of the stimulation pulses (e.g., unipolar, bipolar, combipolar (e.g., using unipolar leads in the atrium and ventricle and performing atrial sensing in a bipolar way using the ventricular lead tip as an indifferent electrode), etc.) by selectively closing the appropriate combination of switches (not shown) as is known in the art. The switch also switches among the various LV electrodes.

Atrial sensing circuits 182 (controlled by a control signal 186) and ventricular sensing circuits 184 (controlled by a control signal 188) may also be selectively coupled to RA lead 120, LV lead 124, and RV lead 130, through switch 174 for detecting the presence of cardiac activity in each of the four chambers of the heart. Accordingly, the atrial (ATR. SENSE) and ventricular (VTR. SENSE) sensing circuits, 182 and 184, may include dedicated sense amplifiers, multiplexed amplifiers or shared amplifiers. Switch 174 determines the "sensing polarity" of the cardiac signal by selectively closing the appropriate switches, as is also known in the art. In this way, a clinician may program the sensing polarity independent of the stimulation polarity. Each sensing circuit, 182 and 184, preferably employs one or more low power, precision amplifiers with programmable gain and/or automatic gain control, bandpass filtering, and a threshold detection circuit, as known in the art, to selectively sense the cardiac signal of interest. The automatic gain control enables pacemaker/ICD 100 to deal effectively with the difficult problem of sensing the low amplitude signal characteristics of atrial or ventricular fibrillation. The outputs of the atrial and ventricular sensing circuits, 182 and 184, are connected to the microcontroller 160 which, in turn, are able to trigger or inhibit the atrial and ventricular pulse generators, 170 and 172, respectively, in a demand fashion in response to the absence or presence of cardiac activity in the appropriate chambers of the heart.

Cardiac signals are applied to the inputs of an analog-to-digital (A/D) data acquisition system 190 (controlled by a control signal 192). Data acquisition system 190 is configured to acquire intracardiac electrogram signals, convert the raw analog data into a digital signal, and store the digital signals for later processing and/or telemetric transmission to an external programmer device 104 or a bedside monitor 102 or personal advisory module. Data acquisition system 190 is coupled to RA lead 120, LV lead 124, and RV lead 130 through switch 174 to sample cardiac signals across any pair of desired electrodes. Microcontroller 160 is further coupled to a memory 194 by a suitable data/address bus 196, wherein the programmable operating parameters used by microcontroller 160 are stored and modified, as required, in order to customize the operation of pacemaker/ICD 100 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each pacing and shocking pulse to be delivered to the patient's heart within each respective tier of therapy. Other pacing parameters include base rate, rest rate and circadian base rate.

Advantageously, the operating parameters of implantable pacemaker/ICD 100 may be non-invasively programmed into memory 194 through a telemetry circuit 101 in telemetric communication with external programmer device 104 or bedside monitor 102, such as a programmer, transtelephonic transceiver, or a diagnostic system analyzer. The telemetry circuit 101 is activated by the microcontroller by a control signal 106. Telemetry circuit 101 advantageously allows intracardiac electrograms and status information relating to the operation of pacemaker/ICD 100 (as contained in microcontroller 160 or memory 194) to be sent to external programmer device 104 and/or bedside monitor 102 through an established communication link 103. An internal warning device 121 (also referred to as a patient alert) may be provided for generating perceptible warning signals to the patient via vibration, voltage or other methods.

Pacemaker/ICD 100 further includes an accelerometer or other physiologic sensor 108, commonly referred to as a "rate-responsive" sensor because it is typically used to adjust pacing stimulation rate according to the exercise state of the patient. Pacemaker/ICD 100 additionally includes a battery 110 that provides operating power to the circuits shown in FIG. 1B. As further shown in FIG. 1B, pacemaker/ICD 100 is shown as having an impedance measuring circuit 112, which is enabled by the microcontroller 160 via a control signal 114. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. Impedance measuring circuit 112 is advantageously coupled to switch 174 so that any desired electrode may be used.

In the case where pacemaker/ICD 100 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, microcontroller 160 further controls a shocking circuit 173 by way of a control signal 179. Shocking circuit 173 generates shocking pulses of low (up to 0.1 joules), moderate (0.1-10 joules) or high energy (11 to 40 joules or more), as controlled by the microcontroller 160. Such shocking pulses are applied to the heart of the patient through at least two shocking electrodes, and as shown in this embodiment, selected from LA coil electrode 128, RV coil electrode 136, and/or SVC coil electrode 138. Housing 140 may act as an active electrode in combination with RV coil electrode 136, or as part of a split electrical vector using SVC coil electrode 138 or LA coil electrode 128 using RV coil electrode 136 as a common electrode).

In this embodiment, microcontroller 160 further includes temporary induced dyssynchrony (TID) controller 197. TID controller 197 controls pacemaker/ICD 100 to deliver a combination of TID therapy (e.g., pacemaker-induced transient asynchrony (PITA) therapy) and cardiac resynchronization therapy (CRT) (including biventricular (BiV) pacing and/or multipoint pacing (MPP)). The combination of TID therapy and CRT facilitates improving cardiac function for a patient.

When TID therapy is used in patients without existing asynchrony, it is generally necessary to cause asynchrony using right ventricular (RV) pacing. However, in patients with existing dyssynchrony, CRT pacing may be used to synchronize the heart, and simply stopping CRT pacing may cause dyssynchrony. Over time, the cardiac function of a patient subjected to CRT pacing may improve the underlying synchrony of the patent will improve). Accordingly, it may be necessary to add asynchrony (instead of merely stopping CRT pacing) using RV pacing to achieve the benefits of TID therapy in such patients. This is analogous to increasing exercise intensity as fitness of an individual improves over time.

Accordingly, the systems and method described herein facilitate applying the TID therapy in patients undergoing CRT. Further, the embodiments described herein include various pacing protocols to achieve a long-term progression of therapy such that, as patent synchronicity changes, the pacing therapy is adjusted to facilitate maximizing benefits. This progression may be achieved by applying more or less severe applications of TID therapy as needed (e.g., by changing the amount of difference in the states between which the patient transitions, as described herein).

In the embodiments described herein, TID controller 197 controls pacemaker/ICD 100 to deliver a plurality of therapy protocols of varying intensity and options. The therapy protocols may be associated with a predetermined period of time (e.g., days, weeks, months, etc.).

For example, in some embodiments, TID controller 197 is programmed to control pacemaker/ICD 100 to deliver the following five treatment protocols. The intensity of the TID therapy for each protocol increases in the order they are listed, with the first protocol having the least intensity and the fifth protocol having the highest intensity. Control pacemaker/ICD 100 may gradually transition between different therapies in the following protocols.

A first example protocol ("Example Protocol A") includes delivering MPP during a first time period, and delivering BiV pacing during a second time period. In some embodiments, the first time period is during the day (e.g., from 6 AM to 10 PM), and the second time period is during the night (e.g., from 10 PM to 6 AM). In some embodiments, the first time period is longer in duration than the second time period. In other embodiments, the first and second time periods may be any time periods having any suitable duration that enables TID controller 197 and pacemaker/ICD 100 to function as described herein. Typically, for CRT, MPP may improve synchrony more than BiV pacing. Accordingly, for a patient with underlying dyssynchrony, the BiV pacing during the second time period is more dyssynchronous than the MPP during the first time period, resulting in relatively low-intensity TID therapy.

A second example protocol ("Example Protocol B") includes delivering CRT during a first time period (including BiV pacing and/or MPP), and delivering no pacing during a second time period. In some embodiments, the first time period is during the day (e.g., from 6 AM to 10 PM), and the second time period is during the night (e.g., from 10 PM to 6 AM). In some embodiments, the first time period is longer in duration than the second time period. In other embodiments, the first and second time periods may be any time periods having any suitable duration that enables TID controller 197 and pacemaker/ICD 100 to function as described herein. For a patient with underlying dyssynchrony, the lack of pacing during the second time period results in higher dyssynchrony than the CRT during the first time period.

A third example protocol ("Example Protocol C") includes delivering BiV pacing during a first time period, and delivering RV pacing during a second time period. In some embodiments, the first time period is during the day (e.g., from 6 AM to 10 PM), and the second time period is during the night (e.g., from 10 PM to 6 AM). In some embodiments, the first time period is longer in duration than the second time period. In other embodiments, the first and second time periods may be any time periods having any suitable duration that enables TID controller 197 and pacemaker/ICD 100 to function as described herein. The RV pacing during the second time period results in higher dyssynchrony than the BiV pacing during the first time period.

A fourth example protocol ("Example Protocol D") includes delivering MPP during a first time period, and delivering RV pacing during a second time period. In some embodiments, the first time period is during the day (e.g., from 6 AM to 10 PM), and the second time period is during the night (e.g., from 10 PM to 6 AM). In some embodiments, the first time period is longer in duration than the second time period. In other embodiments, the first and second time periods may be any time periods having any suitable duration that enables TID controller 197 and pacemaker/ICD 100 to function as described herein. The RV pacing during the second time period results in higher dyssynchrony than the MPP during the first time period.

A fifth example protocol ("Example Protocol E") includes delivering BiV pacing during a first time period, delivering MPP for a second time period, and delivering RV pacing during a third time period. In some embodiments, the first time period is during the day (e.g., from 6 AM to 6 PM), the second time period is during the evening (e.g., from 6 PM to 10 PM), and the third time period is during the night (e.g., from 10 PM to 6 AM). In some embodiments, the first time period is longer in duration than the second time period and/or the third time period. The second time period may be longer, equal, or shorter in duration than the third time period. In other embodiments, the first, second, and third time periods may be any time periods having any suitable duration that enables TID controller 197 and pacemaker/ICD 100 to function as described herein. The RV pacing during the third time period results in higher dyssynchrony than the BiV pacing and MPP during the first and second time periods. Furthermore, MPP may cause higher battery drain than BiV pacing. Accordingly, in some cases, it may be preferable to provide BiV pacing (rather than MPP) for long periods of time (e.g., the first period of time). Example Protocol E enables using the battery-saving BiV pacing while providing the increased transition intensity (e.g., from MPP to RV pacing) by delivering MPP for the second time period between BiV pacing and RV pacing.

Over relatively long periods of time (e.g., over a period of several weeks), multiple different protocols (such as the example protocols described above) may be transitioned through in sequence. Transitions between different protocols may be triggered, for example, after the current protocol has been active for a predetermined period of time (e.g., weeks). Alternatively, transitions may be triggered based on an indicator of patient status (e.g., based on QRS width, hemodynamics, arrhythmia, etc.). Alternatively, transitions may be triggered manually by the patient or a clinician.

Figure 2:
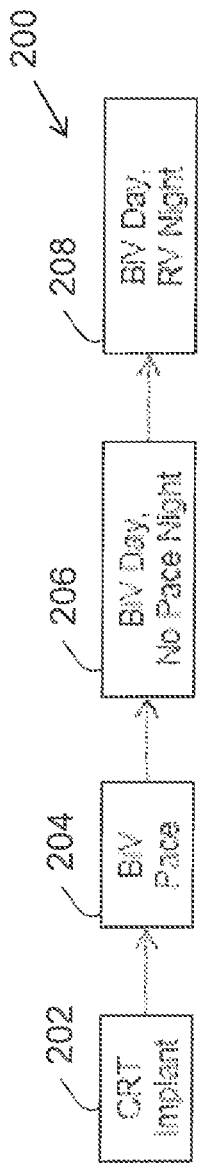
FIG. 2 shows a first example protocol sequence that may be implemented using the implantable stimulation device shown in FIGS. 1A and 1B.
Figure 3:
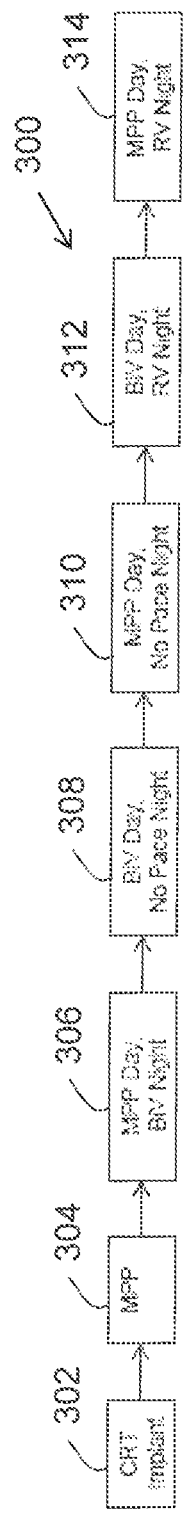
FIG. 3 shows a second example protocol sequence that may be implemented using the implantable stimulation device shown in FIGS. 1A and 1B.
Figure 4:
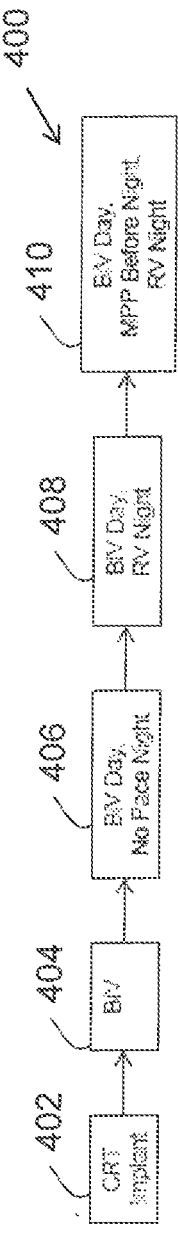
FIG. 4 shows a third example protocol sequence that may be implemented using the implantable stimulation device shown in FIGS. 1A and 1B.

FIGS. 2-4 show three different example sequences of protocols. A first example protocol sequence 200 is shown in FIG. 2. First protocol sequence 200 begins, in the illustrated embodiment, with an implant 202 of a CRT-enabled device, such as the pacemaker/ICD 100 (shown in FIGS. 1A and 1B). The implanted pacemaker/ICD 100 is configured to provide the therapy protocols in first protocol sequence 200.

First protocol sequence 200 includes a first protocol 204, such as BiV pacing and/or MPP pacing. For instance, first protocol 204 may include only BiV pacing substantially continuously or only MPP substantially continuously. Alternatively, first protocol 204 may include Example Protocol A described above, including providing MPP during a first period of time and providing BiV during a second period of time.

After a predetermined period of time (e.g., days, weeks, etc.), first protocol sequence 200 transitions from first protocol 204 to a second protocol 206. Second protocol 206 may include Example Protocol B described above, including providing BiV pacing during a first period of time (e.g., during the day) and providing no pacing during a second period of time (e.g., during the night).

After a predetermined period of time (e.g., days, weeks, etc), first protocol sequence 200 transitions from second protocol 206 to a third protocol 208. Third protocol 208 may include Example Protocol C described above, including providing BiV pacing during a first period of time (e.g., during the day) and providing RV pacing during a second period of time (e.g., during the night).

FIG. 3 depicts a second example protocol sequence 300. Similar to first protocol sequence 200, second protocol sequence 300 begins, in the illustrated embodiment, with an implant 302 of a CRT-enabled device, such as the pacemaker/ICD 100 (shown in FIGS. 1A and 1B). The implanted pacemaker/ICD 100 is configured to provide the therapy protocols in second protocol sequence 300.

Second protocol sequence 300 includes a first protocol 304, such as BiV pacing and/or MPP pacing. For instance, first protocol 304 may include only BiV pacing substantially continuously or only MPP substantially continuously.

After a predetermined period of time (e.g., days, weeks, etc.), second protocol sequence 300 transitions from first protocol 304 to a second protocol 306. Second protocol 306 may include Example Protocol A described above, including providing MPP during a first period of time (e.g., during the day) and providing BiV during a second period of time (e.g., during the night).

After a predetermined period of time (e.g., days, weeks, etc.), second protocol sequence 300 transitions from second protocol 306 to a third protocol 308. Third protocol 308 may include one implementation of Example Protocol B described above, including providing BiV pacing during a first period of time (e.g., during the day) and providing no pacing during a second period of time (e.g., during the night).

After a predetermined period of time (e.g., days, weeks, etc.), second protocol sequence 300 transitions from third protocol 308 to a fourth protocol 310. Fourth protocol 310 may include another, more intense implementation of Example Protocol B described above, including providing MPP pacing during a first period of time (e.g., during the day) and providing no pacing during a second period of time (e.g., during the night).

After a predetermined period of time (e.g., days, weeks, etc.), second protocol sequence 300 transitions from fourth protocol 310 to a fifth protocol 312. Fifth protocol 312 may include Example Protocol C described above, including providing BiV pacing during a first period of time (e.g., during the day) and providing RV pacing during a second period of time (e.g., during the night).

After a predetermined period of time (e.g., days, weeks, etc.), second protocol sequence 300 transitions from fifth protocol 312 to a sixth protocol 314. Sixth protocol 314 may include Example Protocol D described above, including providing MPP pacing during a first period of time (e.g., during the day) and providing RV pacing during a second period of time (e.g., during the night).

FIG. 4 depicts a third example protocol sequence 400. Similar to first protocol sequence 200 and second protocol sequence 300, third protocol sequence 400 begins, in the illustrated embodiment, with an implant 402 of a CRT-enabled device, such as the pacemaker/ICD 100 (shown in FIGS. 1A and 1B). The implanted pacemaker/ICD 100 is configured to provide the therapy protocols in third protocol sequence 400.

Third protocol sequence 400 includes a first protocol 404, such as BiV pacing and/or MPP pacing. For instance, first protocol 404 may include only BiV pacing substantially continuously or only MPP substantially continuously. Alternatively, first protocol 404 may include Example Protocol A described above, including providing MPP during a first period of time and providing BiV during a second period of time.

After a predetermined period of time (e.g., days, weeks, etc.), third protocol sequence 400 transitions from first protocol 404 to a second protocol 406. Second protocol 406 may include Example Protocol B described above, including providing CRT pacing (e.g., BiV pacing or MPP) during a first period of time (e.g., during the day) and providing no pacing during a second period of time (e.g., during the night).

After a predetermined period of time (e.g., days, weeks, etc.), third protocol sequence 400 transitions from second protocol 406 to a third protocol 408. Third protocol 408 may include Example Protocol C described above, including providing BiV pacing during a first period of time (e.g., during the day) and providing RV pacing during a second period of time (e.g., during the night).

After a predetermined period of time (e.g., days, weeks, etc.), third protocol sequence 400 transitions from third protocol 408 to a fourth protocol 410. Fourth protocol 410 may include Example Protocol E described above, including providing BiV pacing for a first period of time (e.g., during the day), providing MPP for a second period of time (e.g., during the evening), and providing RV pacing for a third period of time (e.g., during the night).

As described above, the protocols in a protocol sequence 200, 300, 400 may increase in intensity during the course of the protocol sequence 200, 300, 400, such that the provided therapy adapts to provide increased benefits to a patient's heart.

In one embodiment, pacemaker/ICD 100 is configured to monitor how long a particular protocol is being provided to a patient. Pacemaker/ICD 100 is further configured to transition between protocols in a protocol sequence 200, 300, 400 after a current protocol has been active for a predetermined period of time. It should be understood that each protocol within a protocol sequence 200, 300, 400 may be provided for the same predetermined period of time, or for varying predetermined periods of time.

Additionally or alternatively, pacemaker/ICD 100 is configured to monitor one or more patient status indicator(s) (e.g., based on QRS width, hemodynamics, arrhythmia, etc.) while a protocol is being provided to the patient. Pacemaker/ICD 100 is further configured to transition between protocols in a protocol sequence 200, 300, 400 based at least in part on the one more monitored patient status indicator(s). Additionally or alternatively, pacemaker/ICD 100 is configured to receive a user input (e.g., from a physician or the patient) and transition between protocols in a protocol sequence 200, 300, 400 based at least in part on the received user input. Additionally or alternatively, pacemaker/ICD 100 is configured to stop a protocol sequence 200, 300, 400 or reverse a transition within a protocol sequence based at least in part on the received user input.

The systems and methods described herein take advantage of the concept that added beneficial effects of TID therapy, such as PITA therapy, may be experienced when TID therapy is provided in combination with CRT. Accordingly, providing alternating CRT and TID therapies, particularly in protocol sequences of increasing intensity, may facilitate increased beneficial effects in patients' hearts.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An implantable cardiac device for providing cardiac resynchronization therapy (CRT) and temporary induced right ventricle to left ventricle (V-V) dyssynchrony (TID) therapy, the implantable cardiac device comprising:
one or more pulse generators;
a plurality of electrodes coupled to at least one of the one or more pulse generators; and
a controller communicatively coupled to the one or more pulse generators and configured to cause the one or more pulse generators to apply CRT therapy for a first time period and to apply V-V TID therapy for a second time period to a patient's heart via the plurality of electrodes in accordance with at least one protocol.

2. The implantable cardiac device of claim 1, wherein the first time period occurs during the day, and wherein the second time period occurs during the night.

3. The implantable cardiac device of claim 1, wherein multipoint pacing is applied during the first time period, and wherein biventricular pacing is applied during the second time period.

4. The implantable cardiac device of claim 1, wherein at least one of multipoint and biventricular pacing is applied during the first time period, and wherein no pacing is applied during the second time period.

5. The implantable cardiac device of claim 1, wherein biventricular pacing is applied during the first time period, and wherein right ventricular pacing is applied during the second time period.

6. The implantable cardiac device of claim 1, wherein the at least one protocol further includes a third time period occurring between the first time period and the second time period, wherein biventricular pacing is applied during the first time period, wherein multipoint pacing is applied during the third time period, and wherein right ventricular pacing is applied during the second time period.

7. The implantable cardiac device of claim 1, wherein the at least one protocol includes a sequence of protocols.

8. The implantable cardiac device of claim 7, wherein the controller is configured to transition between a first protocol and a second protocol in the sequence of protocols when the first protocol has been active for a predetermined period of time.

9. The implantable cardiac device of claim 7, wherein the controller is configured to transition between a first protocol and a second protocol in the sequence of protocols based at least in part on a patient status indicator.

10. The implantable cardiac device of claim 7, wherein the controller is configured to i) receive a user input, and ii) transition between a first protocol and a second protocol in the sequence of protocols based at least in part on the received user input.

11. An implantable cardiac device comprising:
one or more pulse generators;
a plurality of electrodes, each of the plurality of electrodes being coupled to at least one of the one or more pulse generators;
a memory device; and
a processor communicatively coupled to the memory device and the one or more pulse generators, the processor configured to cause the one or more pulse generators to apply cardiac resynchronization therapy (CRT) for a first time period and temporary induced V-V dyssynchrony (TID) therapy for a second time period to a patient's heart via the plurality of electrodes in accordance with at least one protocol.

12. The computing device of claim 11, wherein the first time period occurs during the day, and wherein the second time period occurs during the night.

13. The computing device of claim 11, wherein the at least one protocol includes a sequence of protocols.

14. The computing device of claim 13, wherein the processor is configured to transition between a first protocol and a second protocol in the sequence of protocols when the first protocol has been active for a predetermined period of time.

15. The computing device of claim 13, wherein the processor is configured to transition between a first protocol and a second protocol in the sequence of protocols based at least in part on a patient status indicator.

16. A method for providing cardiac resynchronization therapy (CRT) and temporary induced V-V dyssynchrony (TID) therapy, the method comprising:
communicatively coupling one or more pulse generators to a controller; and
causing the one or more pulse generators to apply CRT therapy for a first time period and V-V TID therapy for a second time period to a patient's heart via a plurality of electrodes in accordance with at least one protocol.

17. The method of claim 16, wherein the first time period occurs during the day, and wherein the second time period occurs during the night.

18. The method of claim 16, wherein the at least one protocol includes a sequence of protocols.

* * * * *